US012773174B2

(12) United States Patent
Toporek et al.

(10) Patent No.: US 12,773,174 B2
(45) Date of Patent: Oct. 27, 2026

(54) MULTI-MODAL MEDICAL IMAGE REGISTRATION AND ASSOCIATED DEVICES, SYSTEMS, AND METHODS

(71) Applicant: KONINKLIJKE PHILIPS N.V., Eindhoven (NL)

(72) Inventors: Grzegorz Andrzej Toporek, Cambridge, MA (US); Jochen Kruecker, Andover, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 649 days.

(21) Appl. No.: 17/908,042

(22) PCT Filed: Feb. 23, 2021

(86) PCT No.: PCT/EP2021/054361
§ 371 (c)(1),
(2) Date: Aug. 30, 2022

(87) PCT Pub. No.: WO2021/175644
PCT Pub. Date: Sep. 10, 2021

(65) Prior Publication Data
US 2023/0100078 A1 Mar. 30, 2023

Related U.S. Application Data

(60) Provisional application No. 62/985,589, filed on Mar. 5, 2020.

(51) Int. Cl.
*A61B 5/00* (2006.01)
*A61B 5/055* (2006.01)
(Continued)

(52) U.S. Cl.
CPC ............ *A61B 6/5247* (2013.01); *A61B 5/055* (2013.01); *A61B 8/5261* (2013.01);
(Continued)

(58) Field of Classification Search
CPC ... A61B 8/5261; A61B 5/0035; A61B 6/4417; A61B 8/4416; G06T 2207/10081;
(Continued)

(56) References Cited

U.S. PATENT DOCUMENTS

2013/0053679 A1* 2/2013 Owen .................... G06T 7/32
600/443
2014/0270446 A1 9/2014 Vija
(Continued)

FOREIGN PATENT DOCUMENTS

WO 2019166447 A1 9/2019
WO 2020216752 A1 10/2020
WO 2021018749 A1 2/2021

OTHER PUBLICATIONS

Hu, Yipeng, et al. "Weakly-supervised convolutional neural networks for multimodal image registration." Medical image analysis 49 (2018): 1-13. (Year: 2018).*
(Continued)

*Primary Examiner* — Amandeep Saini
*Assistant Examiner* — Denise G Alfonso

(57) ABSTRACT

Multi-modal medical image registration and associated devices, systems, and methods are provided. For example, a method of medical imaging can include: receiving a first image of a patients anatomy in a first imaging modality; receiving a second image of the patients anatomy in a second, different imaging modality; determining a first pose of the first image relative to a reference coordinate system of the patients anatomy; determining a second pose of the second image relative to the reference coordinate system; determining co-registration data between the first image and the second image based on the first pose and the second pose; and outputting, to a display, the first image co-registered with the second image based on the co-registration data.

16 Claims, 11 Drawing Sheets

(51) Int. Cl.
*A61B 6/00* (2006.01)
*A61B 8/00* (2006.01)

(52) U.S. Cl.
CPC ............... *G06T 2207/10081* (2013.01); *G06T 2207/10088* (2013.01); *G06T 2207/30004* (2013.01)

(58) Field of Classification Search
CPC . G06T 2207/10088; G06T 2207/30004; G06T 2207/20084; G06T 7/33; G06N 3/045
See application file for complete search history.

(56) References Cited

U.S. PATENT DOCUMENTS

| | | | | |
|---|---|---|---|---|
| 2017/0014203 | A1* | 1/2017 | De Mathelin .......... | A61B 5/055 |
| 2018/0260950 | A1 | 9/2018 | Samset et al. | |
| 2019/0139236 | A1 | 5/2019 | Cheng et al. | |
| 2022/0104786 | A1* | 4/2022 | Kunio .................... | A61B 5/318 |

OTHER PUBLICATIONS

Ghavami, Nooshin, et al. "Automatic segmentation of prostate MRI using convolutional neural networks: Investigating the impact of network architecture on the accuracy of volume measurement and MRI-ultrasound registration." Medical image analysis 58 (2019): 101558. (Year: 2019).*
International Search Report and Written Opinion for PCT/EP2021/054361; Mailing date: May 31, 2021, 9 pages.

* cited by examiner

MULTI-MODAL MEDICAL IMAGE REGISTRATION AND ASSOCIATED DEVICES, SYSTEMS, AND METHODS

CROSS-REFERENCE TO PRIOR APPLICATIONS

This application is the U.S. National Phase application under 35 U.S.C. § 371 of International Application No. PCT/EP2021/054361, filed on Feb. 23, 2021, which claims the benefit of U.S. Provisional Patent Application No. 62/985,589, filed on Mar. 5, 2020. These applications are hereby incorporated by reference herein.

TECHNICAL FIELD

The present disclosure relates generally to ultrasound imaging. In particular, multi-modal medical image registration includes determining the position and/or orientation of an ultrasound image of an anatomy of interest and an image of the anatomy from a different medical imaging modality (e.g., magnetic resonance or MR, computed tomography or CT, etc.) relative to a reference or standardized local coordinate system of the anatomy and spatially transforming different images.

BACKGROUND

Ultrasound imaging systems are widely used for medical imaging. For example, a medical ultrasound system may include an ultrasound transducer probe coupled to a processing system and one or more display devices. The ultrasound transducer probe may include an array of ultrasound transducer elements that transmit acoustic waves into a patient's body and record acoustic waves reflected from the internal anatomical structures within the patient's body, which may include tissues, blood vessels, and internal organs. The transmission of the acoustic waves and/or the reception of reflected acoustic waves or echo responses can be performed by the same set of ultrasound transducer elements or different sets of ultrasound transducer elements. The processing system can apply beamforming, signal processing, and/or imaging processing to the received echo responses to create an image of the patient's internal anatomical structures. The image may be presented to a clinician in the form of a brightness-mode (B-mode) image, where each pixel of the image is represented by a brightness level or intensity level corresponding to the echo strength.

While ultrasound imaging is a safe and useful tool for diagnostic examination, intervention, and/or treatment, ultrasound imaging is based on hand-held ultrasound probe motion and positioning, and thus lacks the absolute 3-dimensional (3D) reference frame and anatomical context of other imaging modalities such as computed tomography (CT) or magnetic resonance imaging (MRI) may provide. Co-registering and/or fusing two-dimensional (2D) or 3D ultrasound images with other modalities such as CT or MRI may require additional hardware, setup time, and thus may be costly. Additionally, there may be certain constraints on how the ultrasound probe may be used to perform imaging in order to co-register and/or fuse ultrasound images with other modalities. Co-registration between ultrasound images and another imaging modality are typically performed by identifying common fiducials, common anatomical landmarks, and/or based on similarity measurements of image contents. The feature-based or image content-based image registration can be time consuming and may be prone to error.

SUMMARY

There remains a clinical need for improved systems and techniques for providing medical imaging with multi-modal image co-registration. Embodiments of the present disclosure provide techniques for multi-modal medical image co-registration. The disclosed embodiments define a reference or standardized local coordinate system in an anatomy of interest. The reference coordinate system may be represented in a first imaging space of a first imaging modality in one form and represented in a second imaging space of a second imaging modality different from the first imaging modality in another form for multi-modal image co-registration. For instance, the first imaging modality may be two-dimensional (2D) or three-dimensional (3D) ultrasound imaging and the second imaging modality may be 3D magnetic resonance (MR) imaging. The disclosed embodiments utilize a pose-based multi-modal image co-registration technique to co-register a first image of the anatomy in the first imaging modality and a second image of the anatomy in the second imaging modality. In this regard, a medical imaging system may acquire the first image of the anatomy in the first imaging modality using a first imaging system (e.g., an ultrasound imaging system) and acquire the second image of the anatomy in the second imaging modality using a second imaging system (e.g., an MR imaging system). The medical imaging system determines a first pose of the first image relative to the reference coordinate system in the imaging space of the first imaging modality. The medical imaging system determines a second pose of the second image relative to the reference coordinate system in the imaging space of the second imaging modality. The medical imaging system determines a spatial transformation based on the first image pose and the second image pose. The medical system co-registers the first image of the first imaging modality with the second image of the second imaging modality by applying the spatial transformation to the first image or the second image. The co-registered or combined first and second images can be displayed to assist medical imaging examinations and/or medical interventional procedures. In some aspects, the present disclosure may use deep learning prediction techniques for image pose regression in the local reference coordinate system of the anatomy. The disclosed embodiments can be applied to co-register images of any suitable anatomy in two or more imaging modalities.

In some instances, a system for medical imaging includes: a processor circuit in communication with a first imaging system of a first imaging modality and a second imaging system of a second imaging modality different from the first imaging modality, wherein the processor circuit is configured to: receive, from the first imaging system, a first image of a patient's anatomy in the first imaging modality; receive, from the second imaging system, a second image of the patient's anatomy in the second imaging modality; determine a first pose of the first image relative to a reference coordinate system of the patient's anatomy; determine a second pose of the second image relative to the reference coordinate system; determine co-registration data between the first image and the second image based on the first pose and the second pose; and output, to a display in communication with the processor circuit, the first image co-registered with the second image based on the co-registration data.

In some instances, a method of medical imaging includes: receiving, at a processor circuit in communication with a first imaging system of a first imaging modality, a first image of a patient's anatomy in the first imaging modality; receiving, at the processor circuit in communication with a second imaging system of a second imaging modality, a second image of the patient's anatomy in the second imaging modality, the second imaging modality being different from the first imaging modality; determining, at the processor circuit, a first pose of the first image relative to a reference coordinate system of the patient's anatomy; determining, at the processor circuit, a second pose of the second image relative to the reference coordinate system; determining, at the processor circuit, co-registration data between the first image and the second image based on the first pose and the second pose; and outputting, to a display in communication with the processor circuit, the first image co-registered with the second image based on the co-registration data.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which.

DETAILED DESCRIPTION

Figure 1:
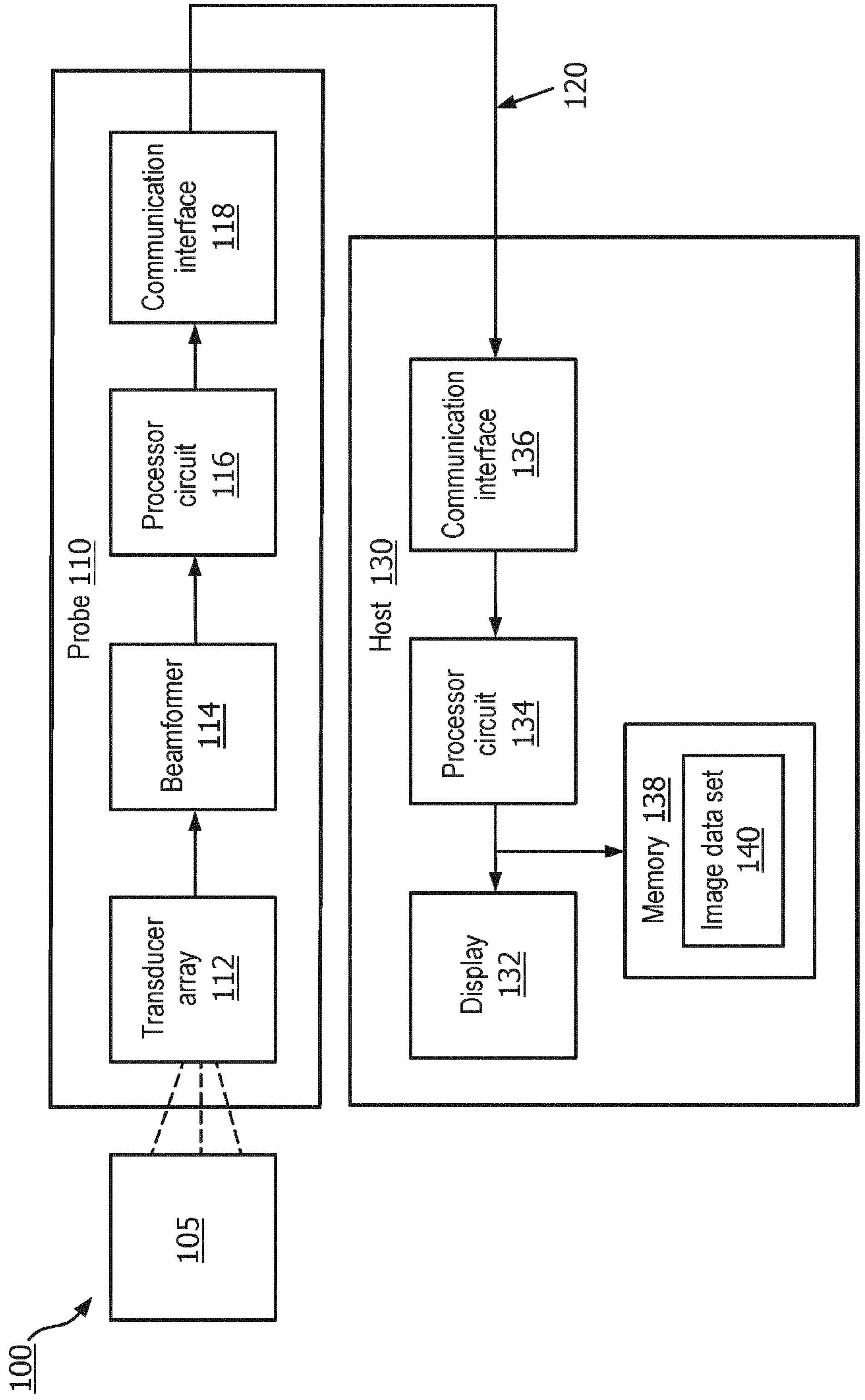
FIG. 1 is a schematic diagram of an ultrasound imaging system, according to aspects of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

FIG. 1 is a schematic diagram of an ultrasound imaging system 100, according to aspects of the present disclosure. The system 100 is used for scanning an area or volume of a patient's body. The system 100 includes an ultrasound imaging probe 110 in communication with a host 130 over a communication interface or link 120. The probe 110 includes a transducer array 112, a beamformer 114, a processor circuit 116, and a communication interface 118. The host 130 includes a display 132, a processor circuit 134, and a communication interface 136.

In an exemplary embodiment, the probe 110 is an external ultrasound imaging device including a housing configured for handheld operation by a user. The transducer array 112 can be configured to obtain ultrasound data while the user grasps the housing of the probe 110 such that the transducer array 112 is positioned adjacent to and/or in contact with a patient's skin. The probe 110 is configured to obtain ultrasound data of anatomy within the patient's body while the probe 110 is positioned outside of the patient's body. In some embodiment, the probe 110 can be an external ultrasound probe suitable for abdominal examination, for example, for diagnosing appendicitis or intussusception.

The transducer array 112 emits ultrasound signals towards an anatomical object 105 of a patient and receives echo signals reflected from the object 105 back to the transducer array 112. The ultrasound transducer array 112 can include any suitable number of acoustic elements, including one or more acoustic elements and/or plurality of acoustic elements. In some instances, the transducer array 112 includes a single acoustic element. In some instances, the transducer array 112 may include an array of acoustic elements with any number of acoustic elements in any suitable configuration. For example, the transducer array 112 can include between 1 acoustic element and 10000 acoustic elements, including values such as 2 acoustic elements, 4 acoustic elements, 36 acoustic elements, 64 acoustic elements, 128 acoustic elements, 500 acoustic elements, 812 acoustic elements, 1000 acoustic elements, 3000 acoustic elements, 8000 acoustic elements, and/or other values both larger and smaller. In some instances, the transducer array 112 may include an array of acoustic elements with any number of acoustic elements in any suitable configuration, such as a linear array, a planar array, a curved array, a curvilinear array, a circumferential array, an annular array, a phased array, a matrix array, a one-dimensional (1D) array, a 1.x dimensional array (e.g., a 1.5D array), or a two-dimensional (2D) array. The array of acoustic elements (e.g., one or more rows, one or more columns, and/or one or more orientations)

that can be uniformly or independently controlled and activated. The transducer array 112 can be configured to obtain one-dimensional, two-dimensional, and/or three-dimensional images of patient anatomy. In some embodiments, the transducer array 112 may include a piezoelectric micromachined ultrasound transducer (PMUT), capacitive micromachined ultrasonic transducer (CMUT), single crystal, lead zirconate titanate (PZT), PZT composite, other suitable transducer types, and/or combinations thereof.

The object 105 may include any anatomy, such as blood vessels, nerve fibers, airways, mitral leaflets, cardiac structure, prostate, abdominal tissue structure, appendix, large intestine (or colon), small intestine, kidney, and/or liver of a patient that is suitable for ultrasound imaging examination. In some aspects, the object 105 may include at least a portion of a patient's large intestine, small intestine, cecum pouch, appendix, terminal ileum, liver, epigastrium, and/or psoas muscle. The present disclosure can be implemented in the context of any number of anatomical locations and tissue types, including without limitation, organs including the liver, heart, kidneys, gall bladder, pancreas, lungs; ducts; intestines; nervous system structures including the brain, dural sac, spinal cord and peripheral nerves; the urinary tract; as well as valves within the blood vessels, blood, chambers or other parts of the heart, abdominal organs, and/or other systems of the body. In some embodiments, the object 105 may include malignancies such as tumors, cysts, lesions, hemorrhages, or blood pools within any part of human anatomy. The anatomy may be a blood vessel, as an artery or a vein of a patient's vascular system, including cardiac vasculature, peripheral vasculature, neural vasculature, renal vasculature, and/or any other suitable lumen inside the body. In addition to natural structures, the present disclosure can be implemented in the context of man-made structures such as, but without limitation, heart valves, stents, shunts, filters, implants and other devices.

The beamformer 114 is coupled to the transducer array 112. The beamformer 114 controls the transducer array 112, for example, for transmission of the ultrasound signals and reception of the ultrasound echo signals. The beamformer 114 provides image signals to the processor circuit 116 based on the response of the received ultrasound echo signals. The beamformer 114 may include multiple stages of beamforming. The beamforming can reduce the number of signal lines for coupling to the processor circuit 116. In some embodiments, the transducer array 112 in combination with the beamformer 114 may be referred to as an ultrasound imaging component.

The processor circuit 116 is coupled to the beamformer 114. The processor circuit 116 may include a central processing unit (CPU), a graphical processing unit (GPU), a digital signal processor (DSP), an application specific integrated circuit (ASIC), a controller, a field programmable gate array (FPGA) device, another hardware device, a firmware device, or any combination thereof configured to perform the operations described herein. The processor circuit 134 may also be implemented as a combination of computing devices, e.g., a combination of a DSP and a microprocessor, a plurality of microprocessors, one or more microprocessors in conjunction with a DSP core, or any other such configuration. The processor circuit 116 is configured to process the beamformed image signals. For example, the processor circuit 116 may perform filtering and/or quadrature demodulation to condition the image signals. The processor circuit 116 and/or 134 can be configured to control the array 112 to obtain ultrasound data associated with the object 105.

The communication interface 118 is coupled to the processor circuit 116. The communication interface 118 may include one or more transmitters, one or more receivers, one or more transceivers, and/or circuitry for transmitting and/or receiving communication signals. The communication interface 118 can include hardware components and/or software components implementing a particular communication protocol suitable for transporting signals over the communication link 120 to the host 130. The communication interface 118 can be referred to as a communication device or a communication interface module.

The communication link 120 may be any suitable communication link. For example, the communication link 120 may be a wired link, such as a universal serial bus (USB) link or an Ethernet link. Alternatively, the communication link 120 nay be a wireless link, such as an ultra-wideband (UWB) link, an Institute of Electrical and Electronics Engineers (IEEE) 802.11 WiFi link, or a Bluetooth link.

At the host 130, the communication interface 136 may receive the image signals. The communication interface 136 may be substantially similar to the communication interface 118. The host 130 may be any suitable computing and display device, such as a workstation, a personal computer (PC), a laptop, a tablet, or a mobile phone.

The processor circuit 134 is coupled to the communication interface 136. The processor circuit 134 may be implemented as a combination of software components and hardware components. The processor circuit 134 may include a central processing unit (CPU), a graphics processing unit (GPU), a digital signal processor (DSP), an application-specific integrated circuit (ASIC), a controller, a FPGA device, another hardware device, a firmware device, or any combination thereof configured to perform the operations described herein. The processor circuit 134 may also be implemented as a combination of computing devices, e.g., a combination of a DSP and a microprocessor, a plurality of microprocessors, one or more microprocessors in conjunction with a DSP core, or any other such configuration. The processor circuit 134 can be configured to generate image data from the image signals received from the probe 110. The processor circuit 134 can apply advanced signal processing and/or image processing techniques to the image signals. In some embodiments, the processor circuit 134 can form three-dimensional (3D) volume image from the image data. In some embodiments, the processor circuit 134 can perform real-time processing on the image data to provide a streaming video of ultrasound images of the object 105.

The display 132 is coupled to the processor circuit 134. The display 132 may be a monitor or any suitable display. The display 132 is configured to display the ultrasound images, image videos, and/or any imaging information of the object 105.

In some aspects, the processor circuit 134 may implement one or more deep learning-based prediction networks trained to predict an orientation of an input ultrasound image relative to a certain coordinate system to assist a sonographer in interpreting the ultrasound image and/or providing co-registration information with another imaging modality, such as computed tomography (CT) or magnetic resonance imaging (MRI), as described in greater detail herein.

In some aspects, the system 100 can be used for collecting ultrasound images to form training data set for deep learning network training. For example, the host 130 may include a memory 138, which may be any suitable storage device, such as a cache memory (e.g., a cache memory of the processor circuit 134), random access memory (RAM), magnetoresistive RAM (MRAM), read-only memory (ROM), programmable read-only memory (PROM), erasable programmable read only memory (EPROM), electrically erasable programmable read only memory (EEPROM), flash memory, solid state memory device, hard disk drives, solid state drives, other forms of volatile and non-volatile memory, or a combination of different types of memory. The memory 138 can be configured to store an image data set 140 to train a deep learning network in predicting image pose relative to a certain reference coordinate system for multi-modal imaging co-registration, as described in greater detail herein.

As discussed above, ultrasound imaging is based on hand-held ultrasound probe motion and positioning, and thus lacks the absolute 3-dimensional (3D) reference frame and anatomical context of other imaging modalities such as CT or MR may provide. Accordingly, it may be helpful to provide a sonographer with co-registration information between ultrasound images and images of another imaging modality such as MR and/or CT. For instance, an ultrasound image may be overlaid on top of a MR 3D image volume based on the co-registration information to assist a sonographer in interpreting the ultrasound image, for example, determining an imaging view of the ultrasound image with respect to the anatomy being imaged.

Figure 2:
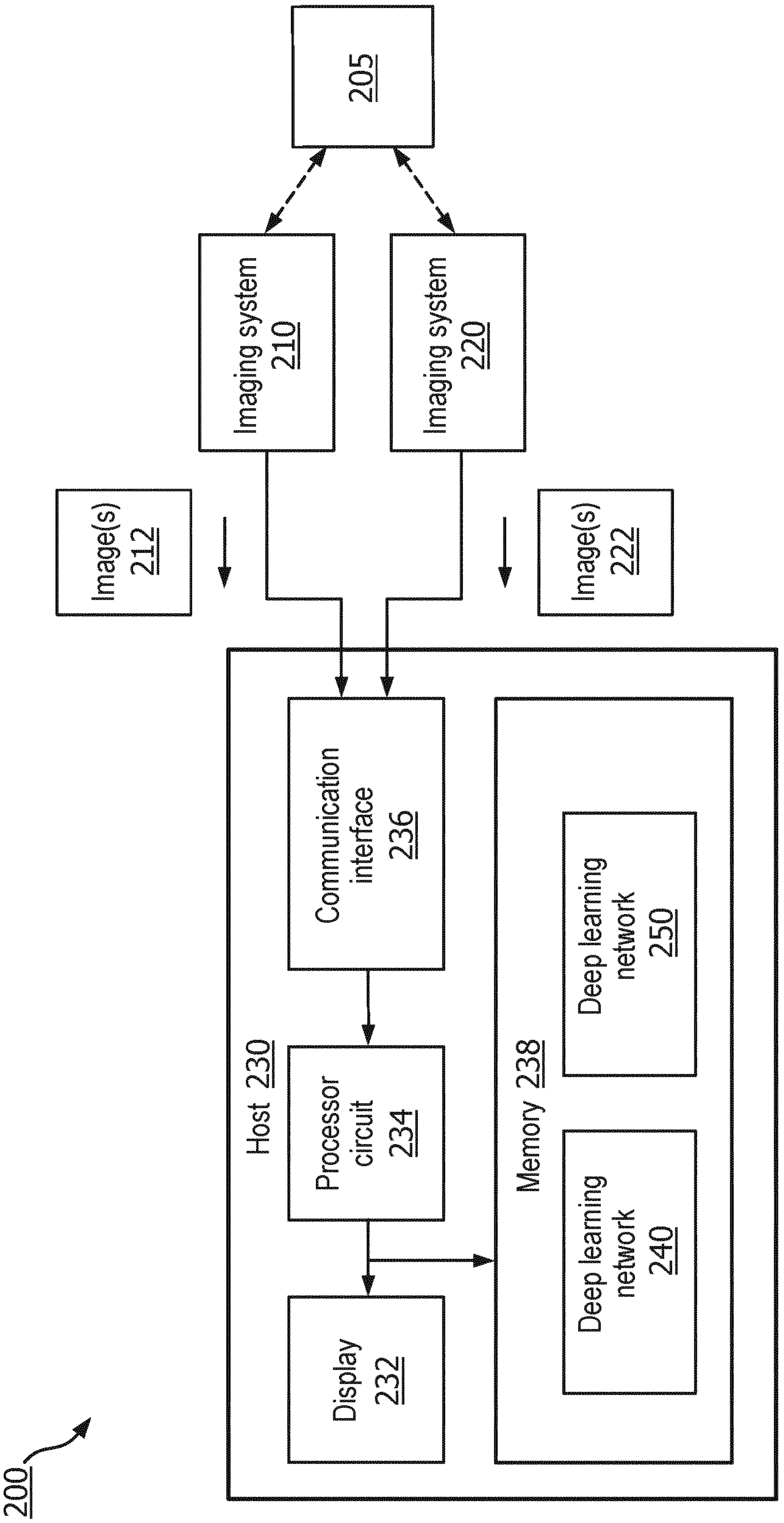
FIG. 2 is a schematic diagram of a multi-modal imaging system, according to aspects of the present disclosure.

FIG. 2 is a schematic diagram of a multi-modal imaging system 200, according to aspects of the present disclosure. The system 200 is used for imaging a patient's anatomy using multiple imaging modalities, such as ultrasound, MR, CT, position emission tomography (PET), single-photon emission tomography (SPEC), cone-beam CT (CBCT), and/or hybrid X-ray systems, and performing image co-registration among the multiple imaging modalities. For simplicity of illustration and discussion, FIG. 2 illustrates the system 200 including two imaging systems, an imaging system 210 of a first imaging modality and another imaging system 220 of a second imaging modality. However, the system 200 may include any suitable number of imaging systems (e.g., about 3 or 4 or more) of different imaging modalities and may perform co-registration among images of the different imaging modalities.

In some aspects, the first imaging modality may be associated with a static image and the second imaging modality may be associated with a moving image. In some other aspects, the first imaging modality may be associated with a moving image and the second imaging modality may be associated with a static image. In yet some other aspects, each of the first imaging modality and the second imaging modality may be associated with moving images or static images. In some aspects, the first imaging modality may be associated with static 3D imaging and the second imaging modality may be associated with moving 3D imaging. In some other aspects, the first imaging modality may be associated with 3D moving imaging and the second imaging modality may be associated with static 3D imaging. In some aspects, the first imaging modality may be associated with 3D imaging and the second imaging modality may be associated with 2D imaging. In some other aspects, the first imaging modality may be associated with 2D imaging and the second imaging modality may be associated with 3D imaging. In some aspects, the first imaging modality is one of ultrasound, MR, CT, PET, SPEC, CBCT, or hybrid X-ray, and the second imaging modality is a different one of the ultrasound, MR, CT, PET, SPEC, CBCT, or hybrid X-ray.

The system 200 further includes a host 230 substantially similar to the host 130. In this regard, the host 230 may include a communication interface 236, a processor circuit 234, a display 232, and a memory 238 substantially similar to the communication interface 136, the processor circuit 134, the display 132, and the memory 138, respectively. The host 230 is communicatively coupled to the imaging systems 210 and 220 via the communication interface 236.

The imaging system 210 is configured to scan and acquire images 212 of a patient's anatomy 205 in the first imaging modality. The imaging system 220 is configured to scan and acquire images 222 of the patient's anatomy 205 in the second imaging modality. The patient's anatomy 205 may be substantially similar to the object 105. The patient's anatomy 205 may include any anatomy, such as blood vessels, nerve fibers, airways, mitral leaflets, cardiac structure, prostate, abdominal tissue structure, appendix, large intestine (or colon), small intestine, kidney, liver, and/or any organ or anatomy that is suitable for imaging in the first imaging modality and in the second imaging modality. In some aspects, the images 212 are 3D image volumes and the images 222 are 3D image volumes. In some aspects, the images 212 are 3D image volumes and the images 222 are 2D image slices. In some aspects, the images 212 are 2D image slices and the images 222 are 3D image volumes.

In some aspects, the imaging system 210 is an ultrasound imaging system similar to the system 100 and the second imaging system 220 is an MR imaging system. Accordingly, the imaging system 210 may acquire and generate the images 212 of the anatomy 205 by emitting ultrasound or acoustic wave towards the anatomy 205 and recording echoes reflected from the anatomy 205 as discussed above with reference to the system 100. The imaging system 220 may acquire and generate the images 222 of the anatomy 205 by applying a magnetic field to force protons of the anatomy 205 to align with that filed, applying radio frequency current to stimulate the protons, stopping the radio frequency current, and detecting energy released as the protons realign. The different scanning and/or image generation mechanisms used in ultrasound and MR imaging may lead to an image 212 and an image 222 representing the same portion of the anatomy 205 in different perspectives or different views (shown in FIGS. 4A-4D).

Accordingly, the present disclosure provides techniques for performing image co-registration between images of different imaging modalities based on poses (e.g., position and/or orientation) of the images of a patient's anatomy (e.g., an organ) with respect to a local reference coordinate system of the patient's anatomy. Since the reference coordinate system is a coordinate system of the anatomy, the reference coordinate system is independent of any imaging modality. In some aspects, the present disclosure may use deep learning prediction techniques to regress the position and/or an orientation of a cross-sectional 2D imaging plane or 2D imaging slice of the anatomy in the local reference coordinate system of the anatomy.

For instance, the processor circuit 234 is configured to receive an image 212 in the first imaging modality from the imaging system 210 and receive an image 222 in the second imaging modality from the imaging system 220. The processor circuit 234 is configured to determine a first pose of the image 212 relative to a reference coordinate system of the patient's anatomy 205, determine a second pose of the image 222 relative to the reference coordinate system of the patient's anatomy 205, and determine a co-registration between the image 212 and the image 222 based on the first pose and the second pose. The processor circuit 234 is further configured to output the image 212 co-registered with the image 222 based on the co-registration to the display 232 for display.

In some aspects, the processor circuit 234 is configured to determine the first pose and the second pose using deep learning prediction techniques. In this regard, the memory 238 is configured to store a deep learning network 240 and a deep learning network 250. The deep learning network 240 can be trained to regress an image pose relative to the reference coordinate system for an input image (e.g., an image 212) in the first imaging modality. The deep learning network 250 can be trained to regress an image pose relative to the reference coordinate system for an input image (e.g., an image 222) in the second imaging modality. The processor circuit 234 is configured to determine the co-registration data by applying the deep learning network 240 and the deep learning network 250 as discussed in greater detail below in FIGS. 3 and 4A-4D.

Figure 3:
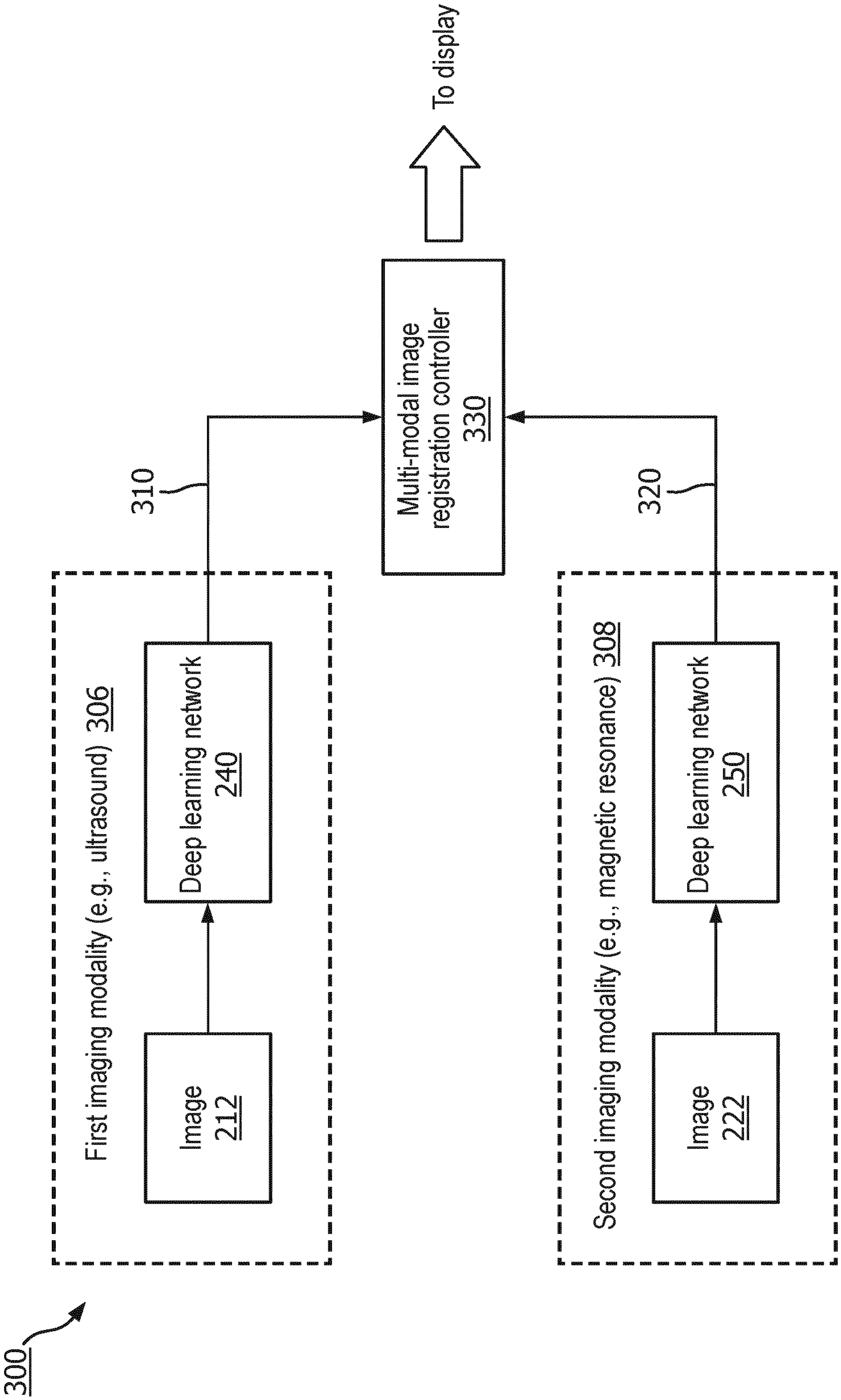
FIG. 3 is a schematic diagram of a multi-modal imaging co-registration scheme, according to aspects of the present disclosure.

FIG. 3 is discussed in relation to FIGS. 4A-4D to illustrate multi-modal image co-registration based on regression of image poses of different imaging modalities in an anatomy coordinate system. FIG. 3 is a schematic diagram of a multi-modal image co-registration scheme 300, according to aspects of the present disclosure. The scheme 300 is implemented by the system 200. In particular, the processor circuit 234 may implement multi-modal image co-registration as shown in the scheme 300. The scheme 300 includes two prediction paths, one path including the deep learning network 240 trained to perform pose regression for the first imaging modality 306 of the imaging system 210 (shown in the top path) and another path including the deep learning network 250 trained to perform pose regression for the second imaging modality 308 of the imaging system 220 (shown in the bottom path). In the illustrated example of FIG. 3, the imaging modality 306 may be ultrasound imaging and the imaging modality 308 may be MR imaging. The scheme 300 further includes a multi-modal image registration controller 330 coupled to the deep learning network 240 and the deep learning network 250. The multi-modal image registration controller 330 may be similar to the processor circuits 134 and 234 and may include hardware and/or software components.

The scheme 300 defines a common reference coordinate system for the anatomy 205 for image co-registration between different imaging modalities. For instance, the deep learning network 240 is trained to receive the input image 212 in the imaging modality 306 and output an image pose 310 of the input image 212 with respect to the common reference coordinate system. Similarly, the deep learning network 250 is trained to receive the input image 222 in the imaging modality 308 and output an image pose 320 of the input image 222 with respect to the common reference coordinate system. The image pose 310 may include a spatial transformation including at least one of a rotational component or a translational component that transform the image 212 from a coordinate system of an imaging space in the first imaging modality to the reference coordinate system. The image pose 320 may include a spatial transformation including at least one of a rotational component or a translational component that transform the image 222 from a coordinate system of an imaging space in the second imaging modality to the reference coordinate system. In some aspects, each of the image pose 310 and image pose 320 include a 6 degree of freedom (6DOF) transformation matrix include 3 rotation components (e.g., indicating an orientation) and 3 translational components (e.g., indicating a position). The different coordinate systems and transformations are discussed below with reference to FIGS. 4A-4D.

FIGS. 4A-4D illustrate the use of a reference coordinate system defined based on a particular feature or portion of a patient's anatomy (e.g., the anatomy) for multi-modal image co-registration as shown in the scheme 300. For simplicity of illustration and discussion, FIGS. 4A-4D illustrate the multi-modal image co-registration of images of a patient's prostate acquired from ultrasound imaging and MR imaging. However, the scheme 300 may be applied to co-register images of any anatomies (e.g., heart, liver, lung, blood vessels, . . . ) acquired in any suitable imaging modalities using similar coordinate system transformations discussed below.

Figure 4B:
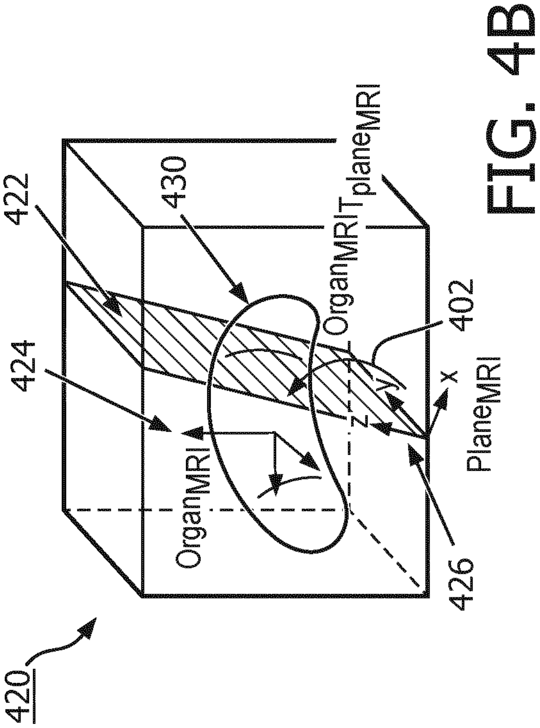
FIG. 4B illustrates a 3D image volume in a magnetic resonance (MR) imaging space, according to aspects of the present disclosure.
Figure 4D:
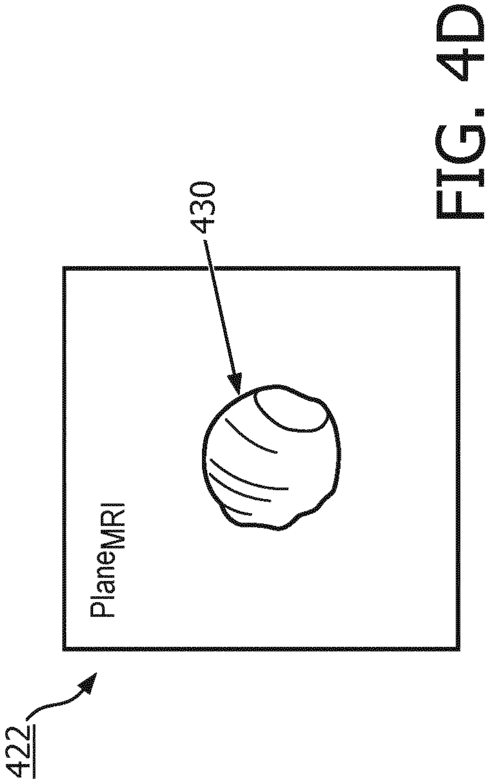
FIG. 4D illustrates a 2D MR image slice, according to aspects of the present disclosure.
Figure 4A:
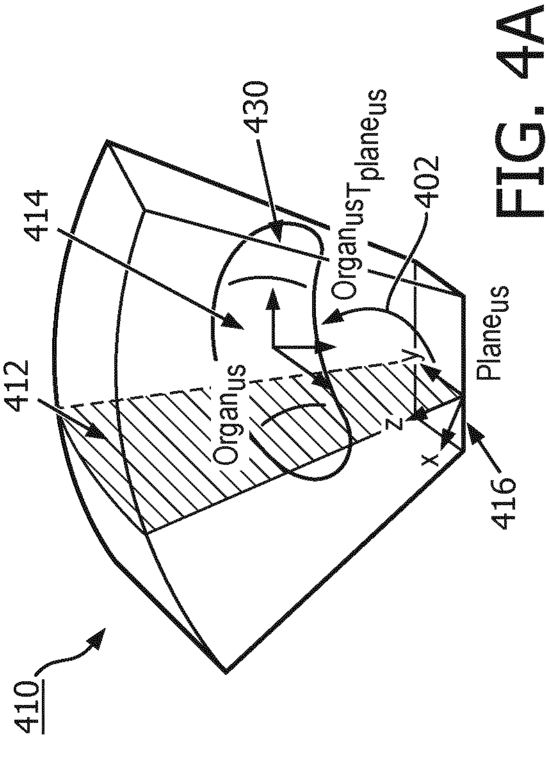
FIG. 4A illustrates a three-dimensional (3D) image volume in an ultrasound imaging space, according to aspects of the present disclosure.

FIG. 4A illustrates a 3D image volume 410 in an ultrasound imaging space, according to aspects of the present disclosure. The 3D image volume 410 includes an image of a prostate 430. The prostate 430 may correspond to the anatomy 205. A reference coordinate system 414 is defined for the prostate 430 in the ultrasound imaging space, denoted as $organ_{US}$. In some aspects, the reference coordinate system 414 may be defined based on a centroid of the prostate 430. For instance, the origin of the reference coordinate system 414 may correspond to the centroid of the prostate 430. Thus, the reference coordinate system 414 is a local coordinate system of the prostate 430.

FIG. 4B illustrates a 3D image volume 420 in an MR imaging space, according to aspects of the present disclosure. The 3D image volume 420 includes an image of the same prostate 430. A reference coordinate system 424 is defined for the prostate 430 in the MR imaging space, denoted as $organ_{MRI}$. The reference coordinate system 424 in the MR imaging space is identical to the reference coordinate system 414 in the ultrasound imaging space. For instance, the origin of the reference coordinate system 424 corresponds to the centroid of the prostate. In this regard, in some instances both reference coordinate systems 414 and 424 are the same because they are defined by the anatomy of the patient (e.g., origin is defined based on the organ of interest). Accordingly, the origins of reference coordinate systems 414 and 424 can have the same location (e.g., centroid in the prostate anatomy) and the x, y, and z axes can be oriented in the same directions (e.g. x axis along the first principal axis of the prostate, and y in supine patient direction). The reference coordinate systems 414 and 424 are depicted in FIGS. 4A-B based on the transrectal ultrasound looking at the prostate from below, while the MRI view is from above (or the side). In other instances, the orientation of the x-y-z axes in the reference coordinate system 424 may be different than x-y-z axes of the reference coordinate system 414. A translation matrix can be utilized to align the x-y-z axes of the reference coordinate systems 414, 424 if different orientations are utilized.

Figure 4C:
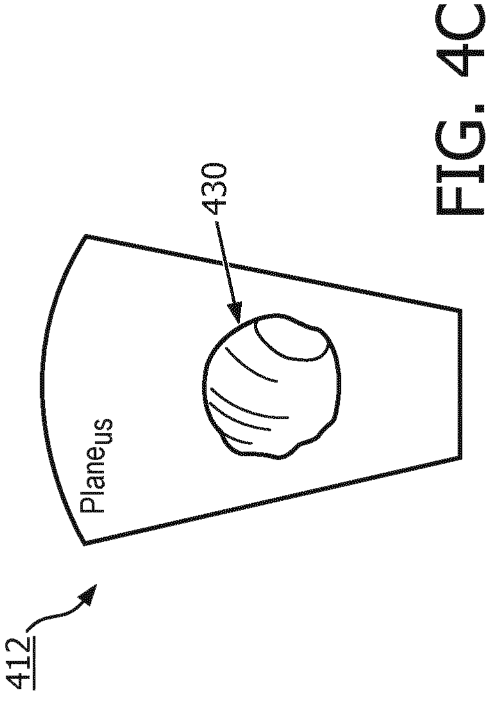
FIG. 4C illustrates a two-dimensional (2D) ultrasound image slice, according to aspects of the present disclosure.

FIG. 4C illustrates a 2D ultrasound image slice 412, denoted as $plane_{US}$, of the 3D image volume 410 in the ultrasound imaging space, according to aspects of the present disclosure. The cross-sectional slice 412 is defined in a coordinate system 416 of the ultrasound imaging space.

FIG. 4D illustrates a 2D MR image slice 422 denoted as $plane_{MRI}$, of the 3D image volume 420 in the MR imaging space, according to aspects of the present disclosure. The cross-sectional slice 422 is in a coordinate system 426 of the MR imaging space.

To illustrate the multi-modal image co-registration in FIG. 3, the image 212 in the scheme 300 may correspond to the 2D image slice 412 and the image 222 in the scheme 300 may correspond to the 2D image slice 422. The deep learning network 240 is trained to regress a pose 310 of the image 212 (of the imaging modality 306) in the local coordinate system of the organ (e.g., the prostate 430). In other words, the deep learning network 240 predicts a transformation 402 between the ultrasound imaging space coordinate system 416 (of the plane$_{US}$) and the local organ reference coordinate system 414 organ$_{US}$. The transformation 402 can be represented by $^{organ_{us}}T_{plane_{us}}$. The pose 310 predicted or estimated by the deep learning network 240 may be represented by $^{organ_{us}}\hat{T}_{plane_{us}}$.

Similarly, the deep learning network 250 is trained to regress a pose 320 of the image 222 (of the imaging modality 308) in the local coordinate system of the organ (e.g., the prostate 430). In other words, the deep learning network 250 predicts a transformation 404 between the MR imaging space coordinate system 426 (of the plane$_{MRI}$) and the local reference coordinate system 424 organ$_{MRI}$. The transformation 404 can be represented by $^{organMR}T_{plane_{MR}}$ The pose 320 predicted or estimated by the deep learning network 250 may be represented by $^{organMR}\hat{T}_{plane_{MR}}$.

The multi-modal image co-registration controller 330 is configured to receive the pose 310 from the deep learning network 240 and receive the pose 320 from the deep learning network 250. The multi-modal image co-registration controller 330 is configured to compute a multi-modal registration matrix (e.g., a spatial transformation matrix) as shown below:

$$^{mri}T_{us}={}^{mri}T_{plane_{mri}}({}^{organ_{mri}}\hat{T}_{plane_{mri}})^{-organ_{mri}}T_{organ_{us}}{}^{organ_{us}}\hat{T}_{plane_{us}}({}^{us}T_{plane_{us}})^{-1}, \quad (1)$$

where $^{mri}T_{us}$ represents multi-modal registration matrix that transforms the coordinate system 416 in the ultrasound imaging space to the coordinate system 426 in the MR imaging space, $^{us}T_{plane_{us}}$ represents a transformation that transforms the ultrasound image slice 412 or the image 212 into the ultrasound coordinate system 416 $^{mri}T_{plane_{mri}}$, represents a transformation that transforms the MR slice 422 or the image 222 into the MR coordinate system 426, and $^{organ_{mri}}T_{organ_{us}}$ represents a transformation from the coordinate system 414 organ$_{US}$ to the coordinate system 424 organ$_{MRI}$. Since the coordinate system 414 and the coordinate system 424 referred to the same local anatomy coordinate system, $^{organ_{mri}}T_{organ_{us}}$ is an identity matrix.

To register the image 212 (e.g., the ultrasound image slice 412) with the image 222 (e.g., the MR image slice 422), the multi-modal image co-registration controller 330 is further configured to perform a spatial transformation on the image 212 by applying the transformation matrix, $^{mri}T_{us}$, in equation (1) to the image 212. The co-registered images 212 and 22 can be displayed (shown in FIG. 9) on a display, such as the display 132 and 232, to assist a clinician in performing imaging and/or medical procedure, such as biopsy, and/or medical therapy.

In some other aspects, the image 212 may be a 3D moving image volume of the imaging modality 306 similar to the ultrasound 3D volume 410 and the image 222 may be a 3D static image volume of the imaging modality 308 similar to the MR 3D volume 420. The multi-modal image co-registration controller 330 is configured to define or select arbitrary 2D slices in the ultrasound image volume 410, define or select arbitrary 2D slices in the MR image volume 420, determine a multi-modal registration matrix as shown in Equation (1) above to co-register each ultrasound image slice with an MR image slice.

In some aspects, the scheme 300 may be applied to co-register images of a patient's heart obtained from different modalities. To co-register images of the heart, the local organ reference coordinate system (e.g., the reference coordinate systems 414 and 424) may be defined by placing an origin in the center of the left ventricle of the heart and the defining x-y axes to be co-planar with the plane defined by a center of the left ventricle, center of the left atrium and center of the right ventricle, where x-axis points from the left to right ventricle, y-axis points from left ventricle towards left atrium, and z-axis is collinear with the normal to the plane. This imaging plane is commonly known as an apical 4-chamber view of the heart.

While the scheme 300 is described in the context of performing co-registration between two imaging modalities, the scheme 300 may be applied to perform co-registration among any suitable number of imaging modalities (e.g., about 3, 4 or more) using substantially similar mechanisms. In general, for each imaging modality, an image pose may be determined for an input image in the imaging modality with respect to the reference coordinate system of the anatomy in the imaging space of the imaging modality and the multi-modal image co-registration controller 330 select a reference image of a primary imaging modality, determine a spatial transformation matrix (as shown in Equation (1)) to co-register an image of each imaging modality with the reference image.

Figure 5:
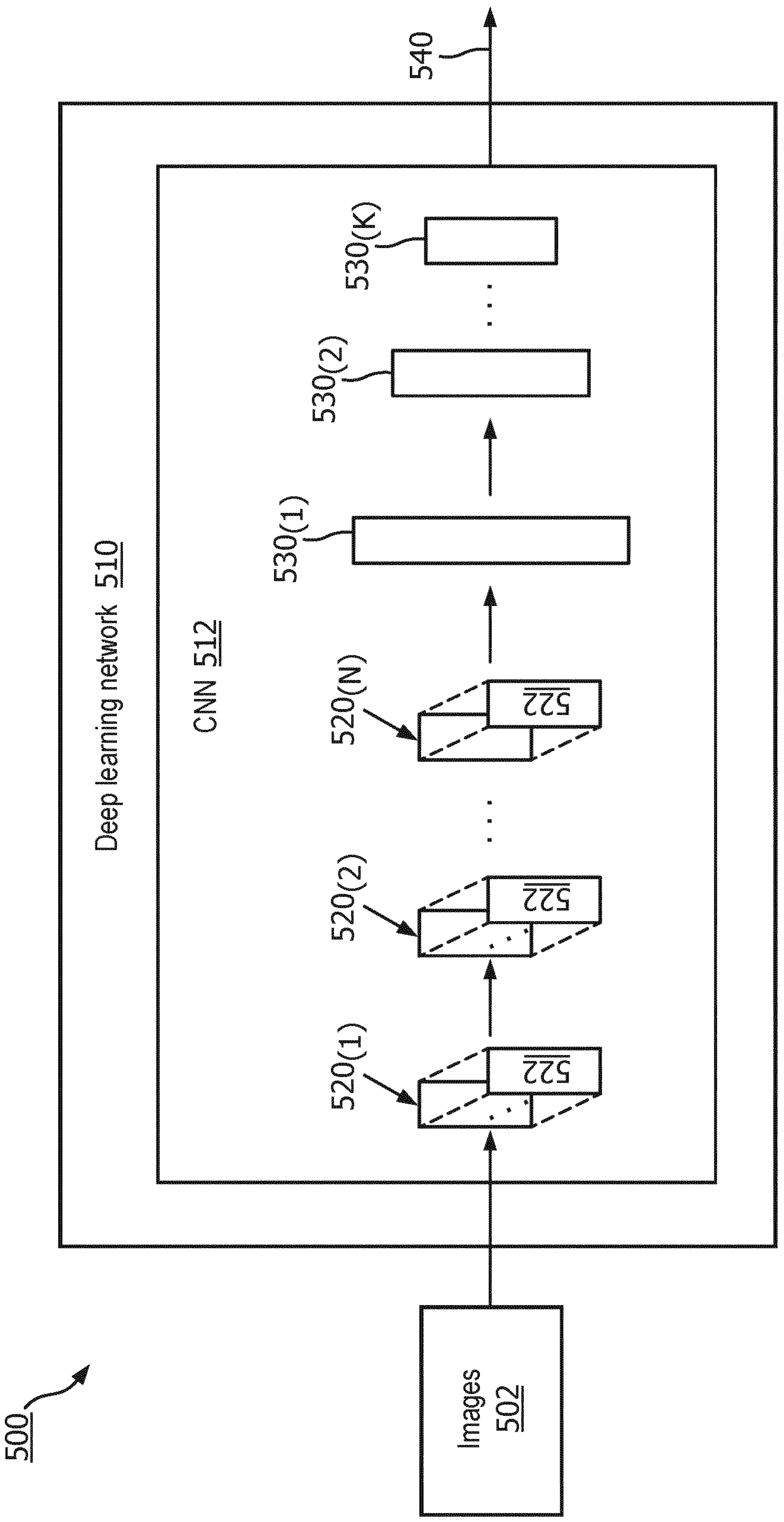
FIG. 5 is a schematic diagram of a deep learning network configuration, according to aspects of the present disclosure.

FIG. 5 is a schematic diagram of a deep learning network configuration 500, according to aspects of the present disclosure. The configuration 500 can be implemented by a deep learning network such as the deep learning network 240 and/or 250. The configuration 500 includes a deep learning network 510 including one or more convolutional neural networks (CNNs) 512. For simplicity of illustration and discussion, FIG. 5 illustrates one CNN 512. However, the embodiments can be scaled to include any suitable number of CNNs 512 (e.g., about 2, 3 or more). The configuration 500 can be trained to regress image pose in a local organ coordinate system (e.g., the reference coordinate systems 414 and 424) for a particular imaging modality as described in greater detail below.

The CNN 512 may include a set of N convolutional layers 520 followed by a set of K fully connected layers 530, where N and K may be any positive integers. The convolutional layers 520 are shown as $\mathbf{520}_{(1)}$ to $\mathbf{520}_{(N)}$. The fully connected layers 530 are shown as $\mathbf{530}_{(1)}$ to $\mathbf{530}_{(K)}$. Each convolutional layer 520 may include a set of filters 522 configured to extract features from an input 502 (e.g., images 212, 222, 412, and/or 422). The values N and K and the size of the filters 522 may vary depending on the embodiments. In some instances, the convolutional layers $\mathbf{520}_{(1)}$ to $\mathbf{520}_{(N)}$ and the fully connected layers $\mathbf{530}_{(1)}$ to $\mathbf{530}_{(K-1)}$ may utilize a non-linear activation function (e.g. ReLU-rectified linear unit) and/or batch normalization and/or dropout and/or pooling. The fully connected layers 530 may be non-linear and may gradually shrink the high-dimensional output to a dimension of the prediction result (e.g., the output 540).

The output 540 may correspond to the poses 310 and/or 320 discussed above with reference to FIG. 3. The output 540 may be a transformation matrix including a rotational component and/or a translational component that may transform the input image 502 from an imaging space (of an imaging modality used for acquiring the input image 502) into the local organ coordinate system.

Figure 6:
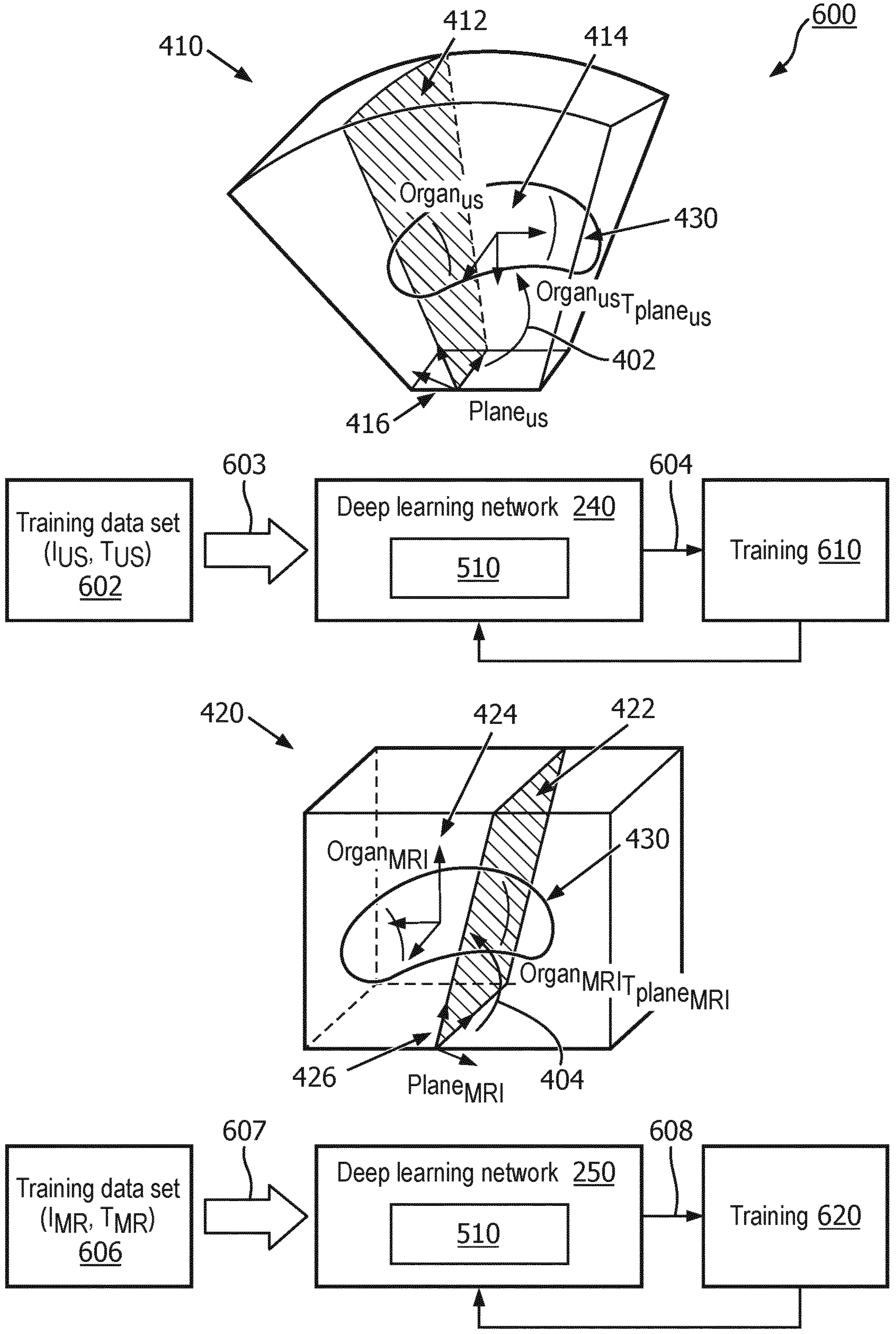
FIG. 6 is a schematic diagram of a deep learning network training scheme, according to aspects of the present disclosure.

FIG. 6 is a schematic diagram of a deep learning network training scheme 600, according to aspects of the present disclosure. The scheme 600 can be implemented by the systems 100 and/or 200. In particular, the scheme 600 may be implemented to train multiple deep learning networks for image pose regression in a reference or organ coordinate system (e.g., the reference coordinate systems 414 and 424). Each deep learning network may be separately trained for a particular imaging modality. For instance, for co-registration between MR images and ultrasound images, one deep learning network may be trained on ultrasound images and another network may be trained on MR images. For simplicity of illustration and discussion, the scheme 600 is discussed in the context of training the deep learning network 240 based on ultrasound images and training the deep learning network 250 based on MR images, where the deep learning networks 240 and 250 are configured as shown in FIG. 5. However, the training scheme 600 may be applied to trained deep learning networks of any network architecture and for any imaging modalities for multi-modal image co-registration.

In the illustrated example of FIG. 6, the deep learning network 240 is trained to regressing poses of ultrasound images of the prostate 430 in the local reference coordinate system 414 of the prostate 430 (show in the top half of FIG. 6). The deep learning network 250 is trained to regressing poses of MR images of the prostate 430 in the local reference coordinate system 424 of the prostate 430 (show in the bottom half of FIG. 6). As discussed above, the local reference coordinate system 414 and the local reference coordinate system 424 correspond to the same reference coordinate system locally at the prostate 430.

To train the network 240, a set of 2D cross-sectional planes or image slices, denoted as $I_{US}$, generated from 3D ultrasound imaging of the prostate 430 is collected. In this regard, 3D ultrasound imaging is used to acquire 3D imaging volume 410 of the prostate 430. The 2D cross-sectional planes (e.g., the 2D ultrasound image slice 412) can be random selected from the 3D imaging volume 410. The 2D cross-sectional planes are defined by a 6DOF transformation matrix $T_{US} \in SE(3)$—describing translation and rotation of the plane—in the local organ coordinate system 414. Each 2D image $I_{US}$ is labelled with the transformation matrix $T_{US}$. Alternatively, 2D ultrasound imaging with tracking can be used to acquire 2D images of the prostate 430 and determine a pose for each image in the local organ coordinate system based on the tracking. The 2D ultrasound imaging can provide higher resolution 2D images than the 2D cross-sectional planes obtained from slicing the 3D imaging volume 410.

The training data set 602 can be generated from the 2D cross-sectional image slices and corresponding transformations to form ultrasound image-transformation pairs. Each pair includes a 2D ultrasound image slice, $I_{US}$, and a corresponding transformation matrix, $T_{US}$, for example, shown as ($I_{US}$, $T_{US}$). For instance, the training data set 602 may include 2D ultrasound images 603 annotated or labelled with a corresponding transformation describing translation and rotation of the image 603 in the local organ coordinate system 414. The labeled image 603 is input to the deep learning network 240 for training. The labelled transformations, $T_{US}$, serve as the ground truths for training the deep learning network 240.

The deep learning network 240 can be applied to each image 603 in the data set 602, for example, using forward propagation, to obtain an output 604 for the input image 603. The training component 610 adjusts the coefficients of the filters 522 in the convolutional layers 520 and weightings in the fully connected layers 530, for example, by using backward propagation to minimize a prediction error (e.g., a difference between the ground truth $T_{US}$ and the prediction result 604). The prediction result 604 may include a transformation matrix, $\hat{T}_{US}$ for transforming the input image 603 into the local reference coordinate system 414 of the prostate 430. In some instances, the training component 610 adjusts the coefficients of the filters 522 in the convolutional layers 520 and weightings in the fully connected layers 530 per input image to minimize the prediction error (between $T_{US}$ and $\hat{T}_{US}$). In some other instances, the training component 610 applies a batch-training process to adjust the coefficients of the filters 522 in the convolutional layers 520 and weightings in the fully connected layers 530 based on a prediction error obtained from a set of input images.

The network 250 may be trained using substantially similar mechanisms as discussed above for the network 240. For instance, the network 250 can be trained on a training data set 606 including 2D MR image slices 607 (e.g., the 2D MR image slice 422) labelled with corresponding transformation matrices $T_{MR}$. The 2D cross-sectional MR image slices 607 can be obtained by randomly selecting 3D cross-sectional planes (multi-planar reconstructions). The 2D cross-sectional MR image slices 607 are defined by a 6DOF transformation matrix $T_{MR} \in SE(3)$—describing translation and rotation of the plane—in the local organ coordinate system 424.

The deep learning network 250 can be applied to each image 607 in the data set 606, for example, using forward propagation, to obtain an output 608 for the input image 607. The training component 620 adjusts the coefficients of the filters 522 in the convolutional layers 520 and weightings in the fully connected layers 530, for example, by using backward propagation to minimize a prediction error (e.g., a difference between the ground truth $T_{MR}$ and the prediction result 604). The prediction result 604 may include a transformation matrix, $\hat{T}_{MR}$, for transforming the input image 607 into the local reference coordinate system 424 of the prostate 430. The training component 620 may adjust the coefficients of the filters 522 in the convolutional layers 520 and weightings in the fully connected layers 530 per input image or per batch of input images.

In some aspects, each of the transformation matrix transformation matrix $T_{US}$ for the ultrasound and the transformation matrix $T_{MR}$ may include a shear component and a scaling component in addition to translation and rotation. Thus, the co-registration between ultrasound and MR may be an affine co-registration instead of a rigid co-registration.

After the deep learning networks 240 and 250 are trained, the scheme 300 may be applied during an application or inference phase for medical examinations and/or guidance. In some aspects, the scheme 300 may be applied to co-register two 3D image volumes of different imaging modalities (e.g., MR and ultrasound), for example, by co-registering 2D image slices of a 3D image volume in one imaging modality with 2D image slices of another 3D image volume in another imaging modality. In some other aspects, instead of using two 3D volumes as input in the application/inference phase, one of the modalities may be a 2D imaging modality, and the images of the 2D imaging modality may be provided for real-time inference of the registration with the other 3D imaging volume of the 3D modality and used for real-time co-display (shown in FIG. 7).

Figure 7:
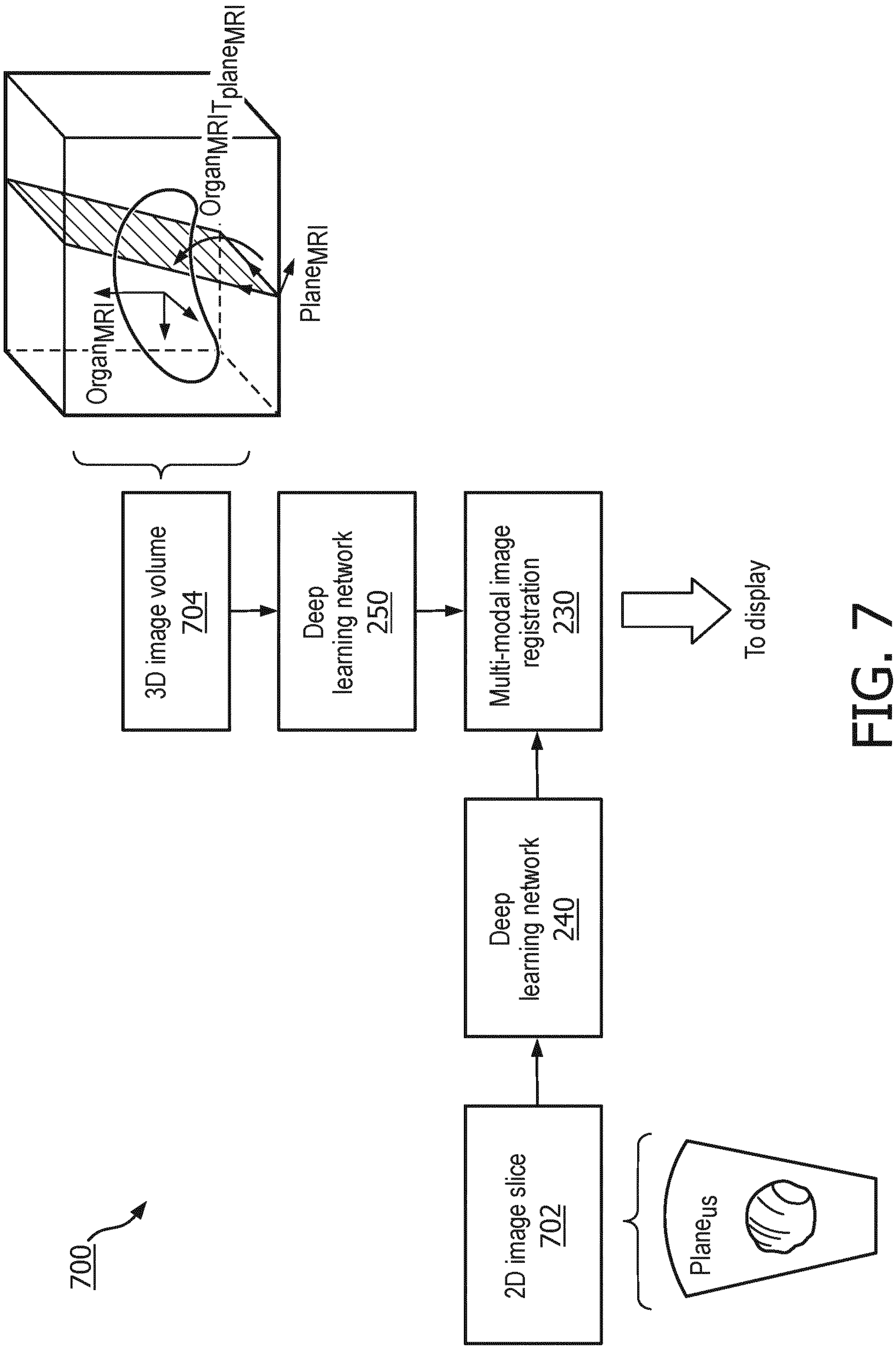
FIG. 7 is a schematic diagram of a multi-modal imaging co-registration scheme, according to aspects of the present disclosure.

FIG. 7 is a schematic diagram of a multi-modal imaging co-registration scheme 700, according to aspects of the present disclosure. The scheme 700 is implemented by the system 200. In particular, the system 200 may provide real-time co-registration of 2D images of a 2D imaging modality with a 3D image volume of a 3D imaging modality, for example, to provide imaging guidance, as shown in the scheme 700. For simplicity of discussion and illustration, the scheme 700 is described in the context of providing real-time co-registration of 2D ultrasound images with 3D MR image volume. However, the scheme 700 can be applied to co-register 2D images of any 2D imaging modality with a 3D image volume of any 3D imaging modality.

In the scheme 700, 2D ultrasound image slices 702 are acquired in real-time, for example, using the imaging system 210 and/or 100 with a probe 110 in a free-hand fashion in arbitrary poses relative to the target organ (e.g., the prostate 430), but within the range of poses extracted from the corresponding 3D ultrasound volumes during training (in the scheme 600). In some other aspects, during the training phase, instead of extracting the large number of cross-sectional slices from a 3D ultrasound volume in an arbitrary manner, the poses of the extracted slices can be tailored to encompass the range of expected poses encountered during real-time scanning in the application phase. The scheme 700 further acquires a 3D MR image volume 704 of the organ, for example, using the imaging system 220 with a MR scanner.

The scheme 700 applies the trained deep learning network 240 to the 2D ultrasound image in real-time to estimate poses of the 2D ultrasound image 702 in the organ coordinate system 414. Similarly, the scheme 700 applies the trained deep learning network 250 to the 3D MR image volume 704 to estimate the transformation of the 3D MR image volume 704 from the MR imaging space to the organ space. In this regard, the 3D MR image volume 704 can be acquired prior to the real-time ultrasound imaging. Thus, the transformation of the 3D MR image volume 704 from the MR imaging space to the organ space can be performed after the 3D MR image volume 704 is acquired and used during the real-time 2D ultrasound imaging for co-registration. In this regard, the scheme 700 applies the multi-modal image co-registration controller 330 to the pose estimations from the 2D ultrasound imaging and the 3D MR imaging to provide a real-time estimate of the pose of the 2D ultrasound image 702 with respect to the pre-acquired MR image volume 704. The multi-modal image co-registration controller 330 may apply Equation (1) above to determine the transformation from ultrasound imaging space to the MR imaging space and perform the co-registration based on the transformation as discussed above with reference to FIG. 3.

Figure 9:
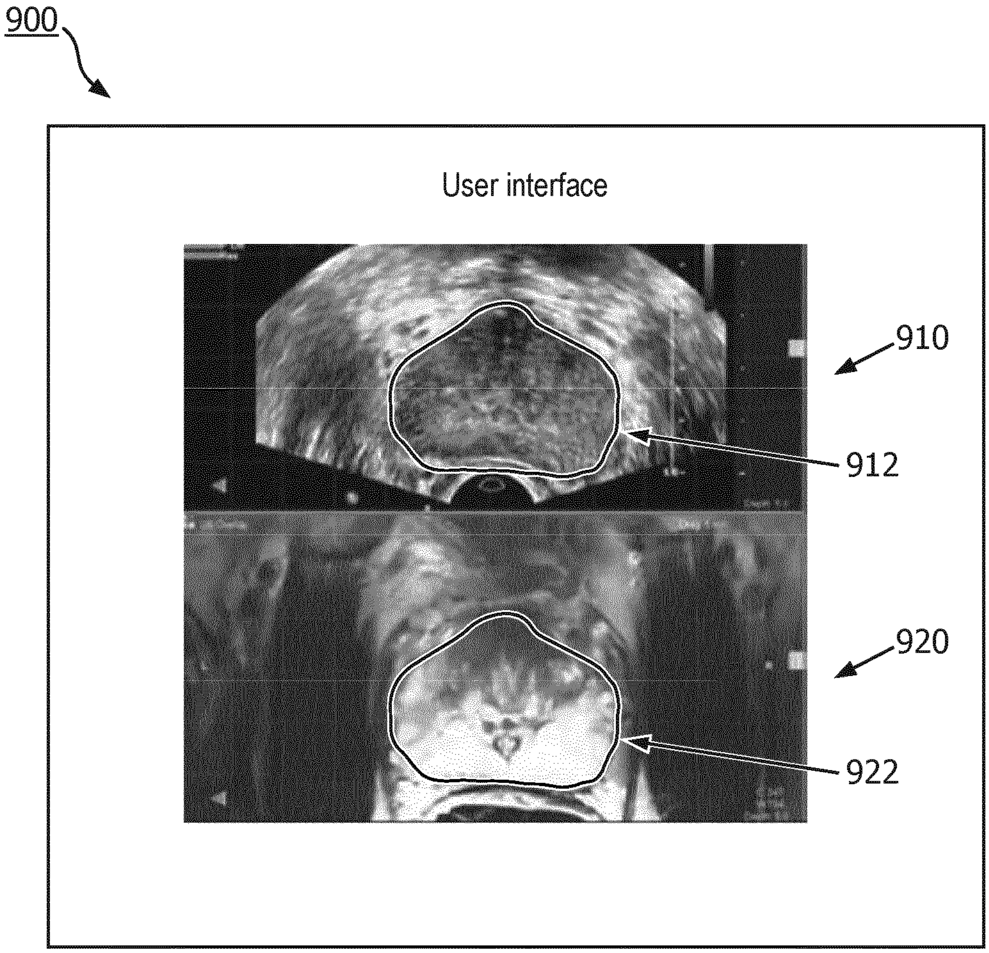
FIG. 9 is a schematic diagram of a user interface for a medical system to provide multi-modal image registration according to aspects of the present disclosure.

The scheme 700 may co-display the 2D ultrasound image 702 with the 3D MR image volume 704 on a display (e.g., the display 132 or 232). For instance, the 2D ultrasound image 702 can be overlaid on top of the 3D MR image volume 704 (as shown in FIG. 9) to provide a clinician performing the real-time 2D imaging positional information of an acquired 2D ultrasound image 702 with respect to the organ under imaging. The positional information can assist the clinician in maneuvering the probe to reach a target imaging view for the ultrasound examination or assist the clinician in performing a medical procedure (e.g., a biopsy).

In some aspects, the pose-based multi-modal image registration discussed above can be used in conjunction with feature-based or image content-based multi-modal image registration or any other multi-modal image registration to provide co-registration with high accuracy and robustness. The accuracy of co-registration may be dependent on the initial pose distance between the images to be registered. For instance, a feature-based or image content-based multi-modal image registration algorithm typically have a “capture range” of initial pose distances, within which the algorithm tends to converge to the correct solution, whereas the algorithm may fail to converge—or converge to an incorrect local minimum—if the initial pose distance is outside the capture range. Thus, the pose-based multi-modal image registration discussed above can be used to align two images of different imaging modalities into a close alignment, for example, satisfying a capture range of a particular feature-based or image content-based multi-modal image registration algorithm, before applying the feature-based or image content-based multi-modal image registration algorithm.

Figure 8:
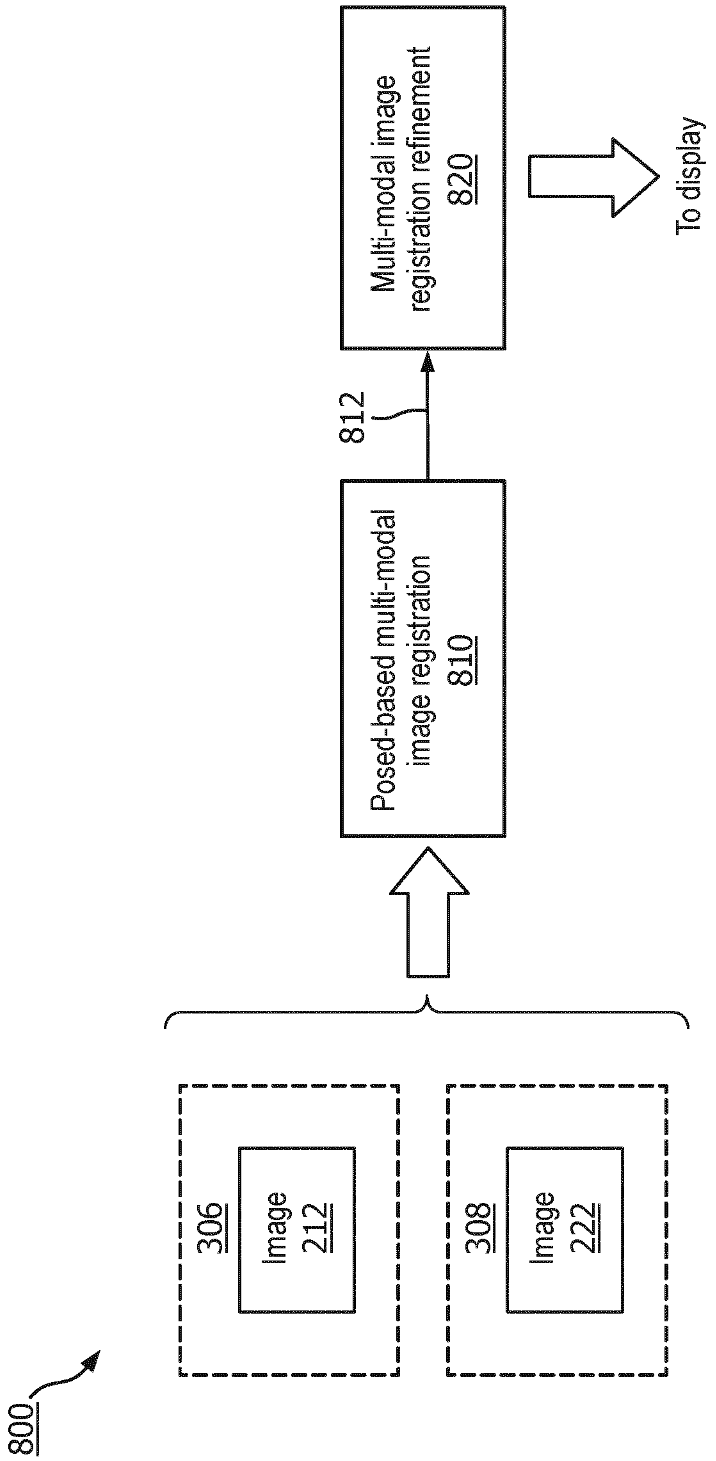
FIG. 8 is a schematic diagram of a multi-modal imaging co-registration scheme, according to aspects of the present disclosure.

FIG. 8 is a schematic diagram of a multi-modal imaging co-registration scheme 800, according to aspects of the present disclosure. The scheme 800 is implemented by the system 200. In particular, the system 200 may apply pose-based multi-modal image registration to align two images of different imaging modalities into a close alignment, followed by applying a multi-modal image registration refinement as shown in the scheme 800 to provide co-registration with high accuracy.

As shown, the scheme 800 applies a posed-based multi-modal image registration 810 to the image 212 of the imaging modality 306 and the image 222 of the imaging modality 308. The posed-based multi-modal image registration 810 may implement the scheme 300 discussed above with reference to FIG. 3. For instance, the pose of the image 212 (e.g., of the prostate 430) is determined with respect to the local organ reference coordinate system (e.g., the reference coordinate system 414) in the imaging space of the imaging modality 306. Similarly, the pose of the image 222 (e.g., of the prostate 430) is determined with respect to the local organ reference coordinate system (e.g., the reference coordinate system 424) in the imaging space of the imaging modality 308. The posed-based multi-modal image registration 810 aligns the image 212 and the image 222 based on the determined poses for the image 212 and the image 222, for example, by performing a spatial transformation to provide a co-registration estimate 812. In some instances, after the spatial transformation, the image 212 may be aligned to the image 222 with a translation misalignment of less than about 30 mm and/or a rotation misalignment of less than about 30 degrees.

After performing the posed-based multi-modal image registration 810, the scheme 800 applies the multi-modal image registration refinement 820 to the co-registered images (e.g., the co-registration estimate 812). In some aspects, the multi-modal image registration refinement 820 may implement a feature-based or image content-based multi-modal image registration, where the registration may be based on a similarity measure (of anatomical features or landmarks) between the images 212 and 222.

In some other aspects, the multi-modal image registration refinement 820 may implement another deep learning-based image co-registration algorithm. For example, automatic multimodal image registration in fusion-guided interventions can be based on iterative predictions from stacked deep learning networks. In some aspects, to train the stacked deep learning networks, the posed-based multi-modal image registration 810 can be applied to the training data set for the stacked deep learning networks to bring image poses of the training data set to be within a certain alignment prior to the training. In some aspects, the prediction errors from the posed-based multi-modal image registration 810 may be calculated, for example, by comparing the predicted registrations to ground truth registrations. The range of pose errors can be modeled with a parameterized distribution, for example, a uniform distribution with minimum and maximum error values for the pose parameters, or a Gaussian distribution with an expected mean and standard deviation for the pose parameters. The pose parameters can be used to generate a training data set with artificially created misaligned registrations between the modalities 306 and 308. The training data set can be used to train the stacked deep learning networks.

FIG. 9 is a schematic diagram of a user interface 900 for a medical system to provide multi-modal image registration according to aspects of the present disclosure. The user interface 900 can be implemented by the system 200. In particular, the system 200 may implement the user interface 900 to provide multi-modal image registration determined from the schemes 300, 700, and/or 800 discussed above with respect to FIGS. 3, 7, and/or 8. The user interface 900 can be displayed on the display 232.

As shown, the user interface 900 includes an ultrasound image 910 and a MR image 920 of the same patient's anatomy. The ultrasound image 910 and the MR image 920 may be displayed based on a co-registration performed using the schemes 300, 700, and/or 800. The user interface 900 further displays an indicator 912 in the image 910 and an indicator 922 in the image 920 according to the co-registration. The indicator 912 may correspond to the indicator 922, but each displayed in a corresponding image according to the co-registration to indicate the same portion of the anatomy in each image 910, 920.

In some other aspects, the user interface 900 may display the image 910 and 920 as color-coded images or checkerboard overlay. For color-coded images, the display may color code different portions of anatomy and uses the same color to represent the same portion on the image 910 and 920. For checkerboard overlay, the user interface 900 may display sub-images of the overlaid image 910 and 920.

Figure 10:
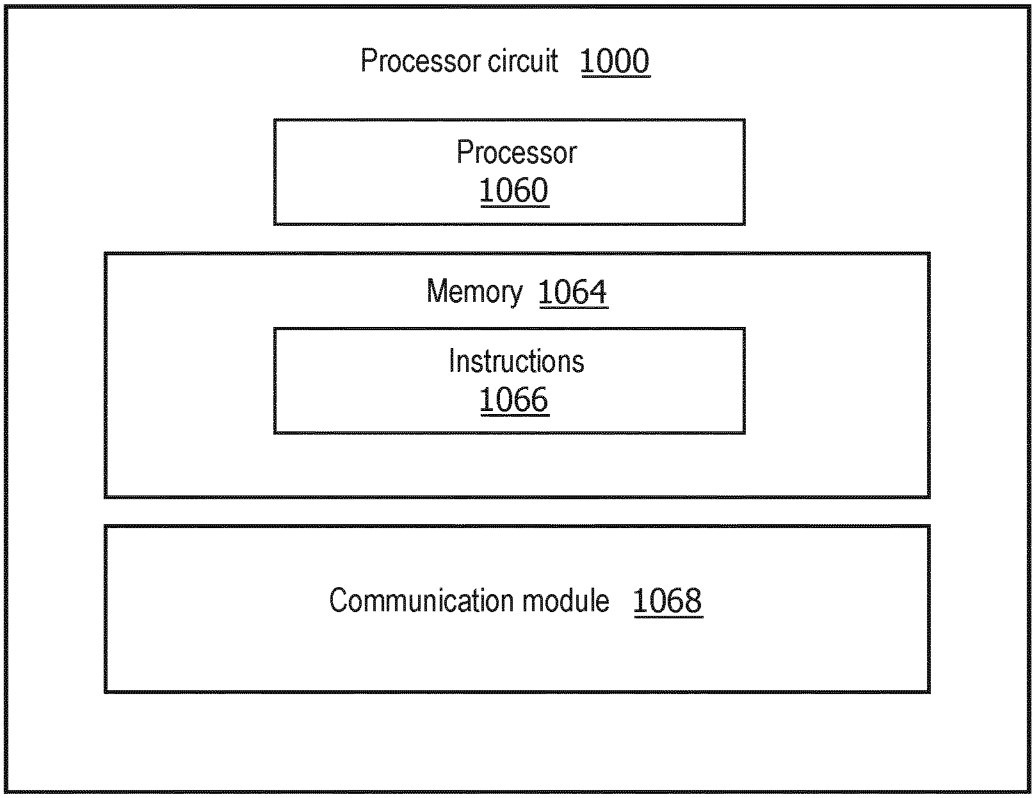
FIG. 10 is a schematic diagram of a processor circuit, according to embodiments of the present disclosure.

FIG. 10 is a schematic diagram of a processor circuit 1000, according to embodiments of the present disclosure. The processor circuit 1000 may be implemented in the probe 110 and/or the host 130 of FIG. 1, the host 230 of FIG. 2, and/or the multi-modal image registration controller 330 of FIG. 3. In an example, the processor circuit 1000 may be in communication with multiple imaging scanners (e.g., the transducer array 112 in the probe 110, a MR image scanners) of different imaging modalities. As shown, the processor circuit 1000 may include a processor 1060, a memory 1064, and a communication module 1068. These elements may be in direct or indirect communication with each other, for example via one or more buses.

The processor 1060 may include a CPU, a GPU, a DSP, an application-specific integrated circuit (ASIC), a controller, an FPGA, another hardware device, a firmware device, or any combination thereof configured to perform the operations described herein, for example, aspects of FIGS. 2-9 and 11. The processor 1060 may also be implemented as a combination of computing devices, e.g., a combination of a DSP and a microprocessor, a plurality of microprocessors, one or more microprocessors in conjunction with a DSP core, or any other such configuration.

The memory 1064 may include a cache memory (e.g., a cache memory of the processor 1060), random access memory (RAM), magnetoresistive RAM (MRAM), read-only memory (ROM), programmable read-only memory (PROM), erasable programmable read only memory (EPROM), electrically erasable programmable read only memory (EEPROM), flash memory, solid state memory device, hard disk drives, other forms of volatile and non-volatile memory, or a combination of different types of memory. In an embodiment, the memory 1064 includes a non-transitory computer-readable medium. The memory 1064 may store instructions 1066. The instructions 1066 may include instructions that, when executed by the processor 1060, cause the processor 1060 to perform the operations described herein, for example, aspects of FIGS. 2-9 and 11 and with reference to the image systems 210 and 220, the host 230 of FIG. 2, and/or the multi-modal image registration controller 330 of FIG. 3. Instructions 1066 may also be referred to as code. The terms "instructions" and "code" should be interpreted broadly to include any type of computer-readable statement(s). For example, the terms "instructions" and "code" may refer to one or more programs, routines, sub-routines, functions, procedures, etc. "Instructions" and "code" may include a single computer-readable statement or many computer-readable statements.

The communication module 1068 can include any electronic circuitry and/or logic circuitry to facilitate direct or indirect communication of data between the processor circuit 1000, image systems 210 and 220 of FIG. 2, the host 230 of FIG. 2, and/or the multi-modal image registration controller 330 of FIG. 3. In that regard, the communication module 1068 can be an input/output (I/O) device. In some instances, the communication module 1068 facilitates direct or indirect communication between various elements of the processor circuit 1000 and/or the image systems 210 and 220, the host 230 of FIG. 2, and/or the multi-modal image registration controller 330 of FIG. 3.

Figure 11:
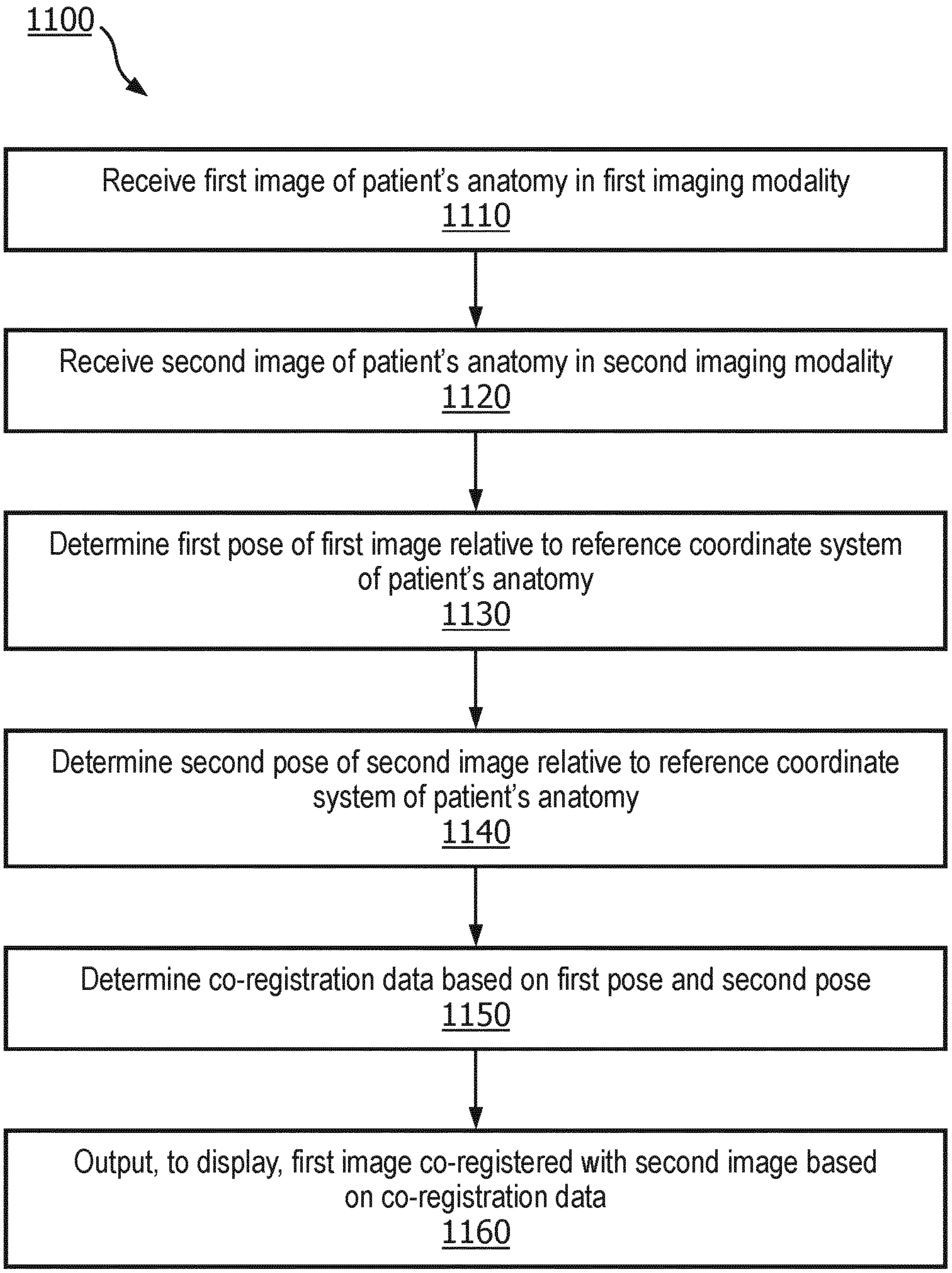
FIG. 11 is a flow diagram of a medical imaging method with multi-modal image co-registration, according to aspects of the present disclosure.

FIG. 11 is a flow diagram of a medical imaging method 1100 with multi-modal image co-registration, according to aspects of the present disclosure. The method 1100 is implemented by the system 200, for example, by a processor circuit such as the processor circuit 1000, and/or other suitable component such as host 230, the processor circuit 234, and/or the multi-modal image registration controller 330. In some examples, the system 200 can include computer-readable medium having program code recorded thereon, the program code comprising code for causing the system 200 to execute the steps of the method 1100. The method 1100 may employ similar mechanisms as in the systems 100 and/or 200 described with respect to FIGS. 1 and 2, respectively, the schemes 300, 600, 700, and/or 800 described with respect to FIGS. 2, 6, 7, and/or 8, respectively, the configuration 500 described with respect to FIG. 5, and/or the user interface 900 described with respect to FIG. 9. As illustrated, the method 1100 includes a number of enumerated steps, but embodiments of the method 1100 may include additional steps before, after, and in between the enumerated steps. In some embodiments, one or more of the enumerated steps may be omitted or performed in a different order.

At step 1110, the method 1100 includes receiving, at a processor circuit (e.g., the processor circuit 1000 and 234) in communication with a first imaging system (e.g., the imaging system 210) of a first imaging modality (e.g., the imaging modality 306), a first image of a patient's anatomy in the first imaging modality.

At step 1120, the method 1100 includes receiving, at the processor circuit in communication with a second imaging system (e.g., the imaging system 220) of a second imaging modality (e.g., the imaging modality 308), a second image of the patient's anatomy in the second imaging modality, the second imaging modality being different from the first imaging modality.

At step 1130, the method 1100 includes determining, at the processor circuit, a first pose (e.g., the pose 310) of the first image relative to a reference coordinate system of the patient's anatomy.

At step 1140, the method 1100 includes determining, at the processor circuit, a second pose (e.g., the pose 320) of the second image relative to the reference coordinate system.

At step 1150, the method 1100 includes determining, at the processor circuit, co-registration data between the first image and the second image based on the first pose and the second pose.

At step 1160, the method 1100 includes outputting, to a display (e.g., the display 132 and/or 232) in communication with the processor circuit, the first image co-registered with the second image based on the co-registration data.

In some aspects, the patient's anatomy includes an organ and the reference coordinate system is associated with a centroid of the organ. The reference coordinate system may also be associated with a center of mass, a vessel bifurcation, a tip or boundary of the organ, a part of a ligament, and/or any other aspects that can be reproducibly identified on medical images across large patient populations.

In some aspects, the step 1130 includes applying a first predictive network (e.g., the deep learning network 240) to the first image, the first predictive network trained based on a set of images of the first imaging modality and corresponding poses relative to the reference coordinate system in an imaging space of the first imaging modality The step 1140 includes applying a second predictive network (e.g., the deep learning network 250) to the second image, the second predictive network trained based on a set of images of the second imaging modality and corresponding poses relative to the reference coordinate system in an imaging space of the second imaging modality.

In some aspects, the first pose includes a first transformation including at least one of a translation or a rotation, and the second pose includes a second transformation including at least one of a translation or a rotation. The step 1150 includes determining a co-registration transformation based on the first transformation and the second transformation. The step 1150 further includes applying the co-registration transformation to the first image to transform the first image into a coordinate system in an imaging space of the second imaging modality. In some aspects, the step 1150 further includes determining the co-registration data further based on the co-registration transformation and a secondary multi-modal co-registration (e.g., the multi-modal image registration refinement 820) between the first image and the second image, where the secondary multi-modal co-registration is based on at least one of an image feature similarity measure or an image pose prediction.

In some aspects, the first image is a 2D image slice or a first 3D image volume, and wherein the second image is a second 3D image volume. In some aspects, the method 1100 includes determining a first 2D image slice from the first 3D image volume and determining a second 2D image slice from the second 3D image volume. The step 1130 includes determining the first pose for the first 2D image slice relative to the reference coordinate system. The step 1140 includes determining the second pose for the second 2D image slice relative to the reference coordinate system.

In some aspects, the method 1100 includes displaying, at the display, the first image with a first indicator (e.g., the indicator 912) and the second image with a second indicator, the first indicator and the second indicator (e.g., the indicator 922) indicating a same portion of the patient's anatomy based on the co-registration data.

Aspects of the present disclosure can provide several benefits. For example, the image pose-based multi-modal image registration may be less challenging and less prone to error than feature-based multi-modal image registration that relies on feature identification and similarity measure. The use of a deep learning-based framework for image pose regression in a local reference coordinate system at an anatomy of interest can provide accurate co-registration results without the dependencies on specific imaging modalities in use. The use of deep learning can also provide a systematic solution that has a lower cost and less time consuming than the feature-based image registration. Additionally, the use of the image pose-based multi-modal image registration to co-register 2D ultrasound images with a 3D imaging volume of a 3D imaging modality (e.g., MR or CT) in real-time can automatically provide spatial position information of an ultrasound probe in use without the use of an external tracking system. The use of the image pose-based multi-modal image registration with the 2D ultrasound imaging in real-time can also provide automatic identification of anatomical information associated with the 2D ultrasound image frame from the 3D imaging volume. The disclosed embodiments can provide clinical benefits such as increased diagnostic confidence, better guidance of interventional procedures, and/or better ability to document findings. In this regard, the ability to compare annotations from pre-operative MRI with the results and findings from intra-operative ultrasound can enhance final reports and/or add confidence to the final diagnosis.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

The invention claimed is:

1. A system for medical imaging, comprising:

a processor circuit in communication with a first imaging system of a first imaging modality and a second imaging system of a second imaging modality different from the first imaging modality, wherein the processor circuit is configured to:

receive, from the first imaging system, a first image of a patient's anatomy in the first imaging modality;

receive, from the second imaging system, a second image of the patient's anatomy in the second imaging modality;

determine a first pose of a first two-dimensional (2D) image slice of the first image relative to a reference coordinate system of the patient's anatomy wherein the first pose is determined by applying a first predictive network to the first 2D image slice of the first image, the first predictive network trained based on a set of images of the first imaging modality and corresponding poses relative to the reference coordinate system in an imaging space of the first imaging modality;

determine a second pose of a second 2D image slice of the second image relative to the reference coordinate system, wherein the second pose is determined by applying a second predictive network to the second 2D image slice of the second image, the second predictive network trained based on a set of images of the second imaging modality and corresponding poses relative to the reference coordinate system in an imaging space of the second imaging modality, wherein the second predictive network is different to the first predictive network;

determine co-registration data between the first image and the second image based on the first pose and the second pose;

output, to a display in communication with the processor circuit, the first image co-registered with the second image based on the co-registration data, wherein the reference coordinate system is associated with an anatomical feature visible in the first image and the second image; and wherein the first imaging modality is ultrasound, and a pose comprises a location, an orientation, or a combination thereof, of an image slice.

2. The system of claim 1, wherein the first pose includes a first transformation including at least one of a translation or a rotation, wherein the second pose includes a second transformation including at least one of a translation or a rotation, and wherein the processor circuit configured to determine the co-registration data is configured to:

determine a co-registration transformation based on the first transformation and the second transformation; and apply the co-registration transformation to the first image to transform the first image into a coordinate system in an imaging space of the second imaging modality.

3. The system of claim 2, wherein the processor circuit configured to determine the co-registration data is configured to:

determine the co-registration data further based on the co-registration transformation and a secondary multi-modal co-registration between the first image and the second image, wherein the secondary multi-modal co-registration is based on at least one of an image feature similarity measure or an image pose prediction.

4. The system of claim 1, wherein the first imaging modality is ultrasound.

5. The system of claim 1, wherein the first imaging modality is one of ultrasound, magnetic resonance (MR), computed tomography (CT), x-ray, position emission tomography (PET), single-photon emission tomography-CT (SPECT), or cone-beam CT (CBCT), and wherein the second imaging modality is a different one of the ultrasound, the MR, the CT, the x-ray, the PET, the SPEC, or the CBCT.

6. The system of claim 1, further comprising the first imaging system and the second imaging system.

7. The system of claim 1, wherein the first image consists of the 2D image slice, and wherein the second image is a three-dimensional (3D) image volume.

8. The system of claim 1, wherein the first image is a first three-dimensional (3D) image volume, and wherein the second image is a second 3D image volume.

9. The system of claim 8, wherein:

the processor circuit is configured to:

determine the first 2D image slice from the first 3D image volume;

determine the second 2D image slice from the second 3D image volume;

the processor circuit configured to determine the first pose is configured to:

determine the first pose for the first 2D image slice relative to the reference coordinate system; and the processor circuit configured to determine the second pose is configured to:

determine the second pose for the second 2D image slice relative to the reference coordinate system.

10. The system of claim 1, further comprising:

the display configured to display the first image with a first indicator and the second image with a second indicator, the first indicator and the second indicator indicating a same portion of the patient's anatomy based on the co-registration data.

11. A method of medical imaging, comprising:

receiving, at a processor circuit in communication with a first imaging system of a first imaging modality, a first image of a patient's anatomy in the first imaging modality;

receiving, at the processor circuit in communication with a second imaging system of a second imaging modality, a second image of the patient's anatomy in the second imaging modality, the second imaging modality being different from the first imaging modality;

determining, at the processor circuit, a first pose of a first two-dimensional (2D) image slice of the first image relative to a reference coordinate system of the patient's anatomy, wherein the first pose is determined by applying a first predictive network to the first 2D image slice of the first image, the first predictive network trained based on a set of images of the first imaging modality and corresponding poses relative to the reference coordinate system in an imaging space of the first imaging modality;

determining, at the processor circuit, a second pose of a second 2D image slice of the second image relative to the reference coordinate system wherein the second pose is determined by applying a second predictive network to the second 2D image slice of the second image, the second predictive network trained based on a set of images of the second imaging modality and corresponding poses relative to the reference coordinate system in an imaging space of the second imaging modality, wherein the second predictive network is different to the first predictive network;

determining, at the processor circuit, co-registration data between the first image and the second image based on the first pose and the second pose; and outputting, to a display in communication with the processor circuit, the first image co-registered with the second image based on the co-registration data, wherein the reference coordinate system is associated with an anatomical feature visible in the first image and the second image; and wherein the first imaging modality is ultrasound, and a pose comprises a location, an orientation, or a combination thereof, of an image slice.

12. The method of claim 11, wherein the first pose includes a first transformation including at least one of a translation or a rotation, wherein the second pose includes a second transformation including at least one of a translation or a rotation, and wherein the determining the co-registration data comprises:

determining a co-registration transformation based on the first transformation and the second transformation; and applying the co-registration transformation to the first image to transform the first image into a coordinate system in an imaging space of the second imaging modality.

13. The method of claim 12, wherein determining the co-registration data comprises:

determining the co-registration data further based on the co-registration transformation and a secondary multi-modal co-registration between the first image and the second image, wherein the secondary multi-modal co-registration is based on at least one of an image feature similarity measure or an image pose prediction.

14. The method of claim 11, wherein the first image consists of the 2D image slice or a first three-dimensional (3D) image volume, and wherein the second image is a second 3D image volume.

15. The method of claim 14, further comprising:

determining the first 2D image slice from the first 3D image volume; and determining the second 2D image slice from the second 3D image volume, wherein the determining the first pose comprises:

determining the first pose for the first 2D image slice relative to the reference coordinate system, and wherein the determining the second pose comprises:

determining the second pose for the second 2D image slice relative to the reference coordinate system.

16. The method of claim 11, further comprising:

displaying, at the display, the first image with a first indicator and the second image with a second indicator, the first indicator and the second indicator indicating a same portion of the patient's anatomy based on the co-registration data.

* * * * *